United States Patent
Wang et al.

(10) Patent No.: US 9,173,969 B2
(45) Date of Patent: Nov. 3, 2015

(54) BIOMATERIAL FOR WOUND HEALING

(75) Inventors: Hui-Min Wang, Kaohsiung (TW);
Mei-Ling Ho, Kaohsiung (TW);
Gwo-Jaw Wang, Kaohsiung (TW);
Je-Ken Chang, Kaohsiung (TW);
Yi-Ting Chou, Kaohsiung (TW);
Ching-Ying Wu, Kaohsiung (TW);
Su-Shin Lee, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 34 days.

(21) Appl. No.: 13/443,996

(22) Filed: Apr. 11, 2012

(65) Prior Publication Data

US 2013/0274190 A1      Oct. 17, 2013

(51) Int. Cl.
| | | |
|---|---|---|
| *A61L 15/28* | (2006.01) | |
| *A61L 27/38* | (2006.01) | |
| *A61L 27/60* | (2006.01) | |
| *A61L 15/32* | (2006.01) | |
| *A61L 15/42* | (2006.01) | |

(52) U.S. Cl.
CPC ............. *A61L 15/28* (2013.01); *A61L 15/32* (2013.01); *A61L 15/325* (2013.01); *A61L 15/425* (2013.01); *A61L 27/3813* (2013.01); *A61L 27/3886* (2013.01); *A61L 27/60* (2013.01)

(58) Field of Classification Search
None
See application file for complete search history.

(56) References Cited

PUBLICATIONS

Choi, 1999, Journal of Biomedical Material Research, vol. 48, pp. 631-639.*
Liu, 2007, Cell Biology International, vol. 31, pp. 985-990.*
Park. Biological characterization of EDC-crosslinked collagen—hyaluronic acid matrix in dermal tissue restoration. 2002, Biomaterials, vol. 24, pp. 1631-1641.*
Choi. Studies on gelatin-containing artifical skin: II. Preparation and characaterization of cross-linked gelatin-hyaluronate sponge. 1999, Journal of Biomedical Material Research, vol. 48, pp. 631-639.*
Bell E., et al., Living tissue formed in vitro and accepted as skin-equivalent tissue of full thickness, Science, 1981, pp. 1052-1054, vol. 211.
Berking C., et al., Basic fibroblast growth factor and ultraviolet B transform melanocytes in human skin, Am J Pathol, 2001, pp. 943-953, vol. 158.
Boyce S. T., Design principles for composition and performance of cultured skin substitutes, Burns, 2001, pp. 523-533, vol. 27.
Choi W., et al., The fibroblast-derived paracrine factor neuregulin-1 has a novel role in regulating the constitutive color and melanocyte function in human skin, J Cell Sci, 2010, pp. 3102-3111, vol. 123.

Dainiak M. B., et al., Gelatin-fibrinogen cryogel dermal matrices for wound repair: preparation, optimisation and in vitro study, Biomaterials, 2010, pp. 67-76, vol. 31.
Duan X., et al., Crosslinking of collagen with dendrimers, J Biomed Mater Res A, 2005, pp. 510-518, vol. 75.
Gordon P. R., et al., Regulation of human melanocyte growth, dendricity, and melanization by keratinocyte derived factors, The Journal of investigative dermatology, 1989, pp. 565-572, vol. 92.
Han J., et al., The cytotoxicity of gamma-secretase inhibitor I to breast cancer cells is mediated by proteasome inhibition, not by gamma-secretase inhibition, Breast Cancer Res, 2009, pp. R57, vol. 11.
Hoeller D., et al., An improved and rapid method to construct skin equivalents from human hair follicles and fibroblasts, Exp Dermatol, 2001, pp. 264-271, vol. 10.
Huang M. H., et al., Evaluation of glucan/poly(vinyl alcohol) blend wound dressing using rat models, Int J Pharm, 2008, pp. 38-46, vol. 346.
Joshi P. G., et al., Melanocyte-keratinocyte interaction induces calcium signalling and melanin transfer to keratinocytes, Pigment Cell Res, 2007, pp. 380-384, vol. 20.
Kim B. M., et al., Cellular artificial skin substitute produced by short period simultaneous culture of fibroblasts and keratinocytes, Br J Plast Surg, 1999, pp. 573-578, vol. 52.
Kremer M., et al., Evaluation of dermal-epidermal skin equivalents ('composite-skin') of human keratinocytes in a collagen-glycosaminoglycan matrix(Integra artificial skin), Br J Plast Surg, 2000, pp. 459-465, vol. 53.
Lee J. E., et al., Characterization of UV-irradiated dense/porous collagen membranes: morphology, enzymatic degradation, and mechanical properties, Yonsei Med J, 2001, pp. 172-179, vol. 42.
Lee S. B., et al., Bio-artificial skin composed of gelatin and (1—>3), (1—>6)-beta-glucan, Biomaterials, 2003, pp. 2503-2511, vol. 24.
Li C. Q., et al., Construction of collagen II/hyaluronate/chondroitin-6-sulfate tri-copolymer scaffold for nucleus pulposus tissue engineering and preliminary analysis of its physico-chemical properties and biocompatibility, J Mater Sci Mater Med, 2010, pp. 741-751, vol. 21.
Ma L, et al., Collagen/chitosan porous scaffolds with improved biostability for skin tissue engineering, Biomaterials, 2003, pp. 4833-4841, vol. 24.
Park S. N., et al., Characterization of porous collagen/hyaluronic acid scaffold modified by 1-ethyl-3-(3-dimethylaminopropyl)carbodiimide cross-linking, Biomaterials, 2002, pp. 1205-1212, vol. 23.

(Continued)

*Primary Examiner* — Prema Mertz
(74) *Attorney, Agent, or Firm* — Hannah M. Tien

(57) ABSTRACT

The present invention provides a biomaterial comprising a scaffold consisting of collagen, hyaluronic acid, and gelatin, which are cross-linked via ethyl-3-[3-dimethylaminopropyl] carbodiimide (EDC) between any two of collagen, hyaluronic acid, and gelatin. The present invention further provides a method for preparing the biomaterial and a method for enhancing wound healing with the biomaterial.

5 Claims, 12 Drawing Sheets
(5 of 12 Drawing Sheet(s) Filed in Color)

(56) References Cited

PUBLICATIONS

Park Y. H., et al., Assessment of dermal toxicity of nanosilica using cultured keratinocytes, a human skin equivalent model and an in vivo model, Toxicology, 2010, pp. 178-181, vol. 267.

Pieper J. S., et al., Development of tailor-made collagen-glycosaminoglycan matrices: EDC/NHS crosslinking, and ultrastructural aspects, Biomaterials, 2000, pp. 581-593, vol. 21.

Regnier M., et al., Integration of Langerhans cells into a pigmented reconstructed human epidermis, J Invest Dermatol, 1997, pp. 510-512, vol. 109.

Schneider A., et al., Self-assembling peptide nanofiber scaffolds accelerate wound healing, PLoS One, 2008, pp. e1410, vol. 3.

Schulz J. T., 3RD, et al., Artificial skin, Annu Rev Med, 2000, pp. 231-244, vol. 51.

Seiberg M., et al., The protease-activated receptor 2 regulates pigmentation via keratinocyte-melanocyte interactions, Exp Cell Res, 2000, pp. 25-32, vol. 254.

Souto L. R., et al., Model for human skin reconstructed in vitro composed of associated dermis and epidermis, Sao Paulo Med J, 2006, pp. 71-76, vol. 124.

Toole B. P., Hyaluronan and its binding proteins, the hyaladherins, Curr Opin Cell Biol, 1990, pp. 839-844, vol. 2.

Usta M., et al., Behavior and properties of neat and filled gelatins, Biomaterials, 2003, pp. 165-172, vol. 24.

Wang T. W., et al., Evaluation and biological characterization of bilayer gelatin/chondroitin-6-sulphate/hyaluronic acid membrane, J Biomed Mater Res B Appl Biomater, 2007, pp. 390-399, vol. 82.

Wu S. C., et al. Enhancement of chondrogenesis of human adipose derived stem cells in a hyaluronan-enriched microenvironment, Biomaterials, 2010, pp. 631-640, vol. 31.

Yamaguchi Y., et al., The regulation of skin pigmentation, J Biol Chem, 2007, pp. 27557-27561, vol. 282.

Yamaguchi Y., et al., Human skin responses to UV radiation: pigment in the upper epidermis protects against DNA damage in the lower epidermis and facilitates apoptosis, FASEB J, 2006, pp. 1486-1488, vol. 20.

Zeeman R., et al., Successive epoxy and carbodiimide cross-linking of dermal sheep collagen, Biomaterials, 1999, pp. 921-931, vol. 20.

* cited by examiner

Collagen (0.6%, w/v, 93.75 μM), HA (0.01%, w/v, 0.05 μM), Gelatin (1%, w/v, 2 mM)

Collagen/HA/Gelatin, pore size=132.5 ± 8.4 μm (A)

(B)

(C)

(A)

Seeding 5 X 10$^6$ FBs within
the scaffold 7 days

Seeding 5 X 10$^5$ MCs and 5 X
10$^6$ KCs within the scaffold 7 days (A)

(B)

BIOMATERIAL FOR WOUND HEALING

FIELD OF THE INVENTION

The present invention relates to a biomaterial comprising a scaffold consisting of collagen, hyaluronic acid, and gelatin, which are cross-linked via ethyl-3-[3-dimethylaminopropyl] carbodiimide (EDC) between any two of collagen, hyaluronic acid, and gelatin. The present invention also relates to a method for preparing the biomaterial and a method for enhancing wound healing with the biomaterial.

DESCRIPTION OF PRIOR ART

The skin, the largest organ in the body of vertebrates, is composed of epidermis and dermis with complex blood and nerve contributions and in the third layer, the hypodermis is composed of lipid and loose connective tissues. These three layers play important roles in preventing the body from many chemical or mechanical damages (Choi et al., *J Cell Sci* 123, 3102-3111 (2010)). Burn patient wounds, in which there is a substantial loss of dermal tissues, heal with wound contractures and the formation of scar tissues. A number of experimental studies deal with new approaches to improve human skin cell growth using either modern physical and pharmacological methods or phytotherapies (Dainiak et al., *Biomaterials* 31, 67-76 (2010)). Because of the antigenicity or the limitation of donor sites, the skin substitutes cannot accomplish the purpose of the skin recovery and yet not be used widely (Bell et al., *Science* 211, 1052-1054 (1981); Schulz et al., *Annu Rev Med* 51, 231-244 (2000); Boyce, *Burns* 27, 523-533 (2001); Ma et al., *Biomaterials* 24, 4833-4841 (2003)). To enhance the growths of skin cells at present is a world-wide costly procedures for each age ranges. Over the last few years, different models for human skin equivalent reconstructed in vitro have been developed, containing associations between dermis (or a dermal equivalent) and epidermis (Kim et al., *Br J Plast Surg* 52, 573-578 (1999); Kremer et al., *Br J Plast Surg* 53, 459-465 (2000); Hoeller et al., *Exp Dermatol* 10, 264-271 (2001); Souto et al., *Sao Paulo Med J* 124, 71-76 (2006)). One crucial factor in skin tissue engineering is the construction of a scaffold.

Collagen is an essential constituent and major compartment of human connective tissues, especially in skin soft tissues (Duan and Sheardown, *J Biomed Mater Res A* 75, 510-518 (2005)). In the past decades, collagen porous scaffolds have been used widely in tissue engineering such as skin, cartilage, bone and nerve where they serve as support and template for cell infiltration, proliferation and differentiation. However, the weak mechanical strength and fast biodegradation rate of the untreated collagen scaffold are the critical problems to limit the applications. Not only is its mechanical strength small or uncontrollable but also its triple-helix structure easily deformed into a random coil structure with heat or biochemical treatments. Cross-linking the collagen-based scaffolds is an efficient manner to optimize the mechanical property and to adjust the biodegradation rate.

Hyaluronic acid (HA) is also a main component of skin, and is related to the tissue repair. It is a biopolymer with a molecular weight larger than 1.0 M kDa containing more than 3,000 repeating units of disaccharides. The polymers are composed of alternating residues of D-glucuronic acid (GlcUA) and N-acetyl-D-glucosamine (GlcNAc) linked by (1→3) bonds as repeating units. In the tissues of the skin, this characteristic is of fundamental importance in water retention (Toole, *Curr Opin Cell Biol* 2, 839-844 (1990)). HA is one of the most hygroscopic molecules present in nature. HA distributes extensively epithelial, neural and connective tissues, being one of the vital components of the extracellular matrix (ECM), supplies notably to cell differentiation and proliferation.

In addition, gelatin, denatured collagen, keeps part of domains for cellular attachment, growth, and differentiation as its native form (Lee et al., *Biomaterials* 24, 2503-2511 (2003)). Furthermore, gelatin has functional groups such as amine and carboxyl groups convenient to modify the surface properties (Usta et al., *Biomaterials* 24, 165-172 (2003)). It contains a large number of glycine, proline and 4-hydroxyproline residues. Cross-linking can be used to adjust degradation rate and biomechanical characteristics (typically to match those characteristics of the tissue designated for regeneration), but it may compromise biocompatibility (Zeeman et al., *Biomaterials* 20, 921-931 (1999)).

Therefore, the cross-linking treatment of collagen/HA/gelatin scaffold has become one of the most important concerns for the bio-porous scaffold. Currently, there are two kinds of cross-linking methods frequently employed in improving the mechanical properties: physical treatments and chemical techniques (Li et al., *J Mater Sci Mater Med* 21, 741-751 (2010)). The former includes the use of photooxidation, dehydrothermal and UV irradiation methods, which could avoid introducing potential cytotoxic chemical residuals and sustain the excellent biocompatibility of collagen materials (Lee et al., *Yonsei Med J* 42, 172-179 (2001)). But most of the physical treatments cannot yield enough high cross-linking degree to meet the demands. So, the treatments by chemical methods are still necessary in most cases. In choosing a cross-linking agent for collagen/HA/gelatin porous scaffold, heterobifunctional agents, which contain 2 different reactive groups that are able to directly link 2 various amino acid side chains, are of interest in maximizing the extent of cross-linking (Pieper et al., *Biomaterials* 21, 581-593 (2000)).

In US patent application No. US 2004/0267362, a connective tissue scaffold comprising anchoring segments, bioresorbable polymeric fibers and a central segment was disclosed. The fibers could be made from collagen, hyaluronic acid, gelatin, and so on. The connective tissue scaffold was useful as an implant to replace or augment damaged or torn connective tissues. However, the requirements of biomaterial for implanting or replacing connective tissue and skin are different. Thus, there remains a need for a biomaterial used for skin engineering application.

In tissue engineering, one vital aims of cell biologists was to stimulate cell growth using sophisticated culture conditions. The performance of skin equivalent depends on cell growth to which they are applied. Much recent evidence has shown that keratinocytes (KCs), melanocytes (MCs) and fibroblasts (FBs) found in the skin to effect mutual cell functions and participated actively in regulating each other (Regnier et al., *J Invest Dermatol* 109, 510-512 (1997); Berking et al., *Am J Pathol* 158, 943-953 (2001); Schneider et al., *PLoS One* 3, e1410 (2008)). For example, melanocytes are affected by external factors such as ultraviolet radiation and also by internal factors secreted from fibroblasts and keratinocytes (Yamaguchi et al., *FASEB J* 20, 1486-1488 (2006)). Besides, some keratinocytes-derived factors enhance the dendricity of isolated melanocytes (Gordon et al., *J Invest Dermatol* 92, 565-572 (1989)). An interesting study revealed that the interactions between melanocytes and keratinocytes plasma membranes induced a transient intracellular calcium signal in keratinocytes that is required for melanosome transfer (Seiberg et al., *Exp Cell Res* 254, 25-32 (2000); Joshi et al., Pigment Cell Res 20, 380-384 (2007); Yamaguchi et al., *J Biol Chem* 282, 27557-27561 (2007)). It also showed that fibroblasts were able to stimulate keratinocytes growth, either by reorganization of collagen matrix or the production of specific growth factors. This reflects that growth factors arising from fibroblasts play an important role on keratinocytes and melanocytes migration, proliferation, and differentiation (Wang et al., *J Biomed Mater Res B Appl Biomater* 82, 390-399 (2007)). A 3-dimension (3D) skin scaffold offers an ECM analog as a required template for a physical support and host infiltration to guide the proliferation and migration of cells into the targeted functional tissues or organs (Park et al., *Biomaterials* 23, 1205-1212 (2002); Park et al., *Toxicology* 267, 178-181 (2010)). An ideal skin scaffold used should possess the characteristics of excellent biocompatibilities, suitable microstructures such as 100~200 μm mean pore size for cell growth and porosities above 90%, controllable biodegradabilities and suitable mechanical properties (Ma et al., *Biomaterials* 24, 4833-4841 (2003)). Therefore, the suitable skin materials are still demanding. There is still a need for a better biomaterial used as bio-supporters to match the qualifications and co-cultures of keratinocytes, melanocytes, and fibroblasts to mimic human normal skin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
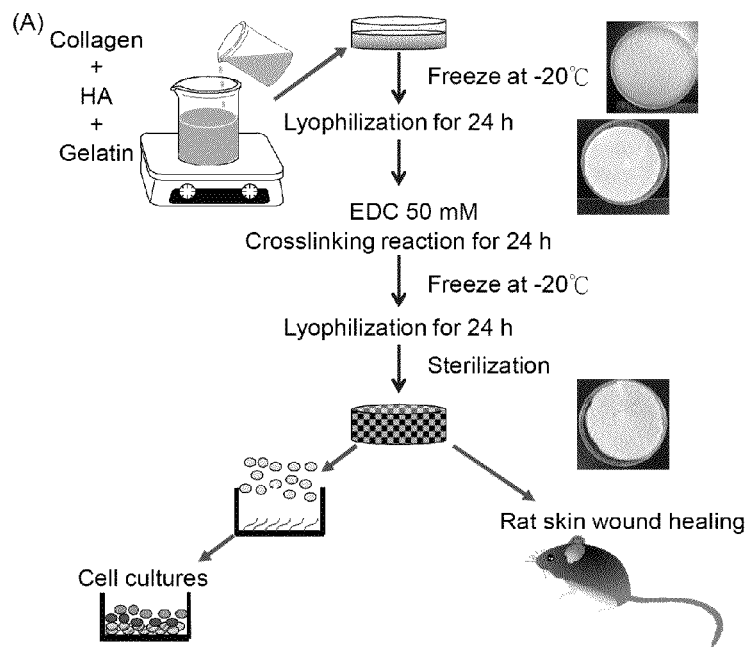
FIG. 1 illustrates the biomaterial manufacture, skin culture and mouse skin wound healing model. (A), (B) Proposed schematic presentation of collagen, hyaluronic acid (HA), and gelatin cross-linked via EDC. (C), (D) SEM of collagen/HA/gelatin scaffolds. The pore size was 132.5±8.4 μm.
Figure 1:
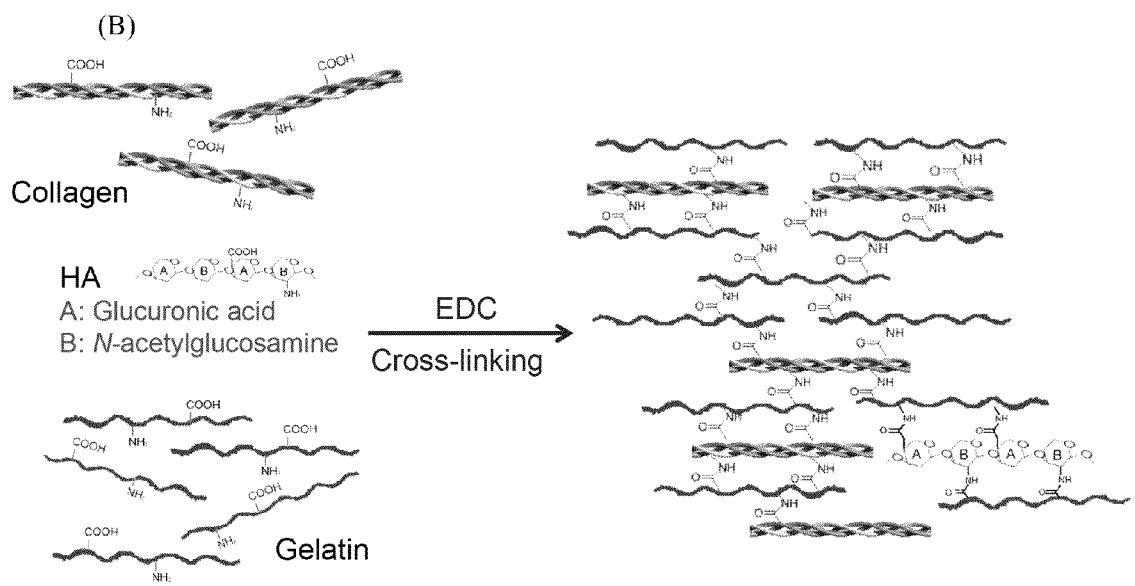
Figure 1:
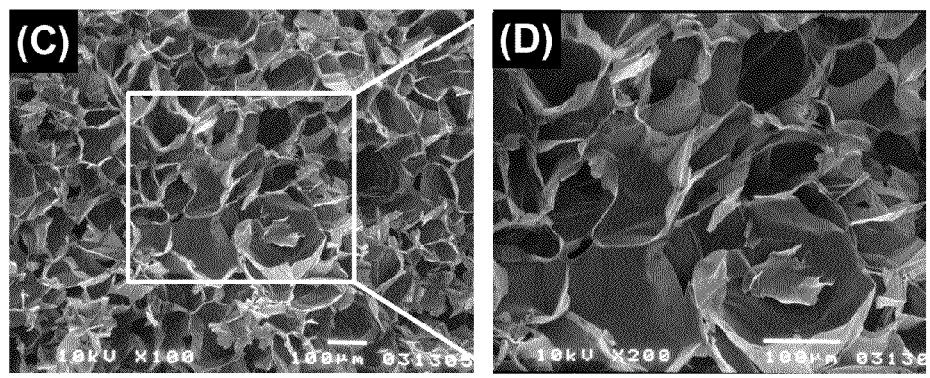

This invention provides a biomaterial comprising a scaffold consisting of collagen, hyaluronic acid, and gelatin, which are cross-linked via ethyl-3-[3-dimethylaminopropyl] carbodiimide (EDC) between any two of collagen, hyaluronic acid, and gelatin.

The present invention also provides a method for preparing the biomaterial, comprising (a) preparing a mixture of collagen, hyaluronic acid, and gelatin; (b) lyophilizing the mixture in step (a); (c) incubating the mixture of step (b) in organic solution containing EDC; (d) removing the mixture from organic solution containing EDC; and (e) lyophilizing the mixture to form the biomaterial.

The present invention further provides a method for enhancing wound healing, comprising covering the biomaterial on a wound.

DETAILED DESCRIPTION OF THE INVENTION

This invention provides a biomaterial comprising a scaffold consisting of collagen, hyaluronic acid, and gelatin, which are cross-linked via ethyl-3-[3-dimethylaminopropyl] carbodiimide (EDC) between any two of collagen, hyaluronic acid, and gelatin. EDC is a heterobifunctional and zero-length cross-linking reagent. It forms a bridge between two amino acids without incorporating itself into the macromolecule of collagen, HA and gelatin. The scaffold having

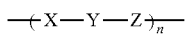

X is gelatin-gelatin, gelatin-collagen, or gelatin-hyaluronic acid; Y is collagen-collagen, collagen-gelatin, or collagen-hyaluronic acid; Z is hyaluronic acid-gelatin, hyaluronic acid-collagen, or hyaluronic acid-hyaluronic acid; n is an integer of 1 or more than 1. The biomaterial is a porous, three-dimensional structure.

The percentage of the collagen is 30% to 45%, the percentage of the hyaluronic acid is 0.1% to 5%, and the percentage of the gelatin is 50% to 70%, provided that total percentage of collagen, hyaluronic acid, and gelatin is 100%. In a preferred embodiment, the pore size in the biomaterial is about 10 to 500 µm. In a more preferred embodiment, the pore size in the biomaterial is about 50 to 200 µm. The selection of crosslinker is important for preparing the porous biomaterial which result in different structure of the biomaterial. The pore size can be varied according to different needs. The thickness of the biomaterial can also be regulated by controlling the volume and percentage of weight/volume concentration of the materials. In one embodiment, the thickness of the biomaterial is about 1 mm in average to mimic the real thickness of epidermis layer and dermis layer of human skin. The biomaterial of the present invention has high water absorption ability. The swelling ratio of the biomaterial is about more than 20 folds of dried scaffold. In a preferred embodiment, the swelling ratio of the biomaterial is more than 25 folds of dried scaffold. Thus, the biomaterial has large porous lamellar matrix spaces to increase their water-containing capacity. The porous morphology after cross-linking provides the possibility that cells can be inoculated into the scaffold. The interconnected pores within the biomaterial provide opportunities of interaction for cytokines and growth factors released by cells, such as keratinocytes, melanocytes and dermal fibroblasts.

The biomaterial of the present invention promotes collagen secretion of fibroblasts. It further reduces the neutrophil infiltration at the wound area and increases the density of epidermis at the wound area. Therefore, the biomaterial of the present invention can be further used for wound healing or artificial skin.

The biomaterial has good biocompatibility. The biomaterial further cultures with fibroblasts, keratinocytes, and melanocytes to form a skin equivalent. The fibroblasts were seeded prior to keratinocytes and melanocytes. The keratinocytes and melanocytes grow and proliferate on the biomaterial with fibroblasts. The three-dimensional structure mimics the physiological environment, which can further used for the skin related experiment, including laboratorial and clinical application. For example, screening large-scale of compounds for studying the interaction with the skin cell and elucidating the regulatory mechanism can be performed by the three-dimensional structure formed by the biomaterial of the present invention.

The present invention also provides a method for preparing the biomaterial of the present invention, comprising: (a) preparing a mixture of collagen, hyaluronic acid, and gelatin; (b) lyophilizing the mixture in step (a); (c) incubating the mixture of step (b) in organic solution containing EDC; (d) removing the mixture from organic solution containing EDC; and (e) lyophilizing the mixture to form the biomaterial. The concentrations of collagen, hyaluronic acid and gelatin in the mixture of step (a) are respectively about 0.5 to 2000 µM, 0.0025 to 1 µM and 0.1 to 40 mM. The concentration of EDC in organic solution is about 2.5 to 1000 mM. The organic solution in the present invention includes but not limited to the following solvent: alkane, alcohol, ketone, ester, ketene and the combination thereof.

In a preferred embodiment, the concentration of collagen is about 10 to 1000 µM, the concentration of hyaluronic acid is about 0.0125 to 0.2 µM and the concentration of gelatin is about 0.5 to 8 mM. In more preferred embodiment, the concentration of collagen is about 50 to 200 µM, the concentration of hyaluronic acid is about 0.025 to 0.1 µM and the concentration of gelatin is about 1 to 4 mM.

In a preferred embodiment, the concentration of EDC in organic solution is about 5 to 500 mM. In a more preferred embodiment, the concentration of EDC in organic solution is about 10 to 250 mM. In another preferred embodiment, the organic solution is ethanol.

The present invention further provides a method for enhancing the wound healing, comprising covering the biomaterial of the present invention on a wound. The biomaterial enhances the wound healing by promoting collagen secretion of fibroblasts, reducing the neutrophil infiltration of the wound and increasing the density of epidermis at the wound.

EXAMPLE

The examples below are non-limiting and are merely representative of various aspects and features of the present invention.

Example 1

Preparing a Biomaterial and Evaluating the Characteristics
Manufacturing a Biomaterial of Collagen/HA/Gelatin Sponge Bio Porousscaffold Collagen (Cat No. C7774, MW: 64,000), gelatin (Cat No. G9539, MW: 5,000) and N-ethyl-N'-[3-dimethylaminopropyl]carbodiimide (EDC) (Cat No. E1769) were all purchased from Sigma-Aldrich Chemical (St. Louis, Mo.). HA (grade FCH-200, MW: 2-2.1 MDa) was obtained from Kibun Food Chemicals (Tokyo, Japan). A solution of collagen/HA/gelatin was mixed with the final concentrations of 93.75 µM, 0.05 µM, and 2 mM, respectively. The mixed solution was poured gently into a 6-cm culture dish and frozen at −20° C. for 48 h. The collagen/HA/gelatin sponge was constructed by lyophilizing the mixed solution for 24 h.

It was then chemically incubated for 24 hours at 25° C. in pure ethanol containing 50 mM EDC. After 24 h, the reaction was terminated by removing EDC solution and was washed with distilled $H_2O$ for several times to remove any un-reacted chemicals (EDC). The scaffold was lyophilized for another 48 hours and was sterilized by ethylene oxide gas. The dried collagen/HA/gelatin scaffold was manufactured in suitable size for further research. FIG. 1 was drawn according to reactions derived from the established reaction paths in homogeneous phase.

Swelling Ratio Assay of the Biomaterial

Scaffold samples of collagen/HA/gelatin (30 mg) were separately immersed into distilled water at 25° C. for 24 h. After removal from the water, the scaffolds were hung up until no dipping water was observed and then weighed. The absorption of water within the swollen scaffold was calculated by the following equation:

$$\text{Water absorption} = (W_w - W_d)/W_d$$

$W_w$ is the weight of the swollen scaffold, and $W_d$ is the weight of the dry scaffold. The results were also compared with four other commercial wound dressings.

Figure 2:
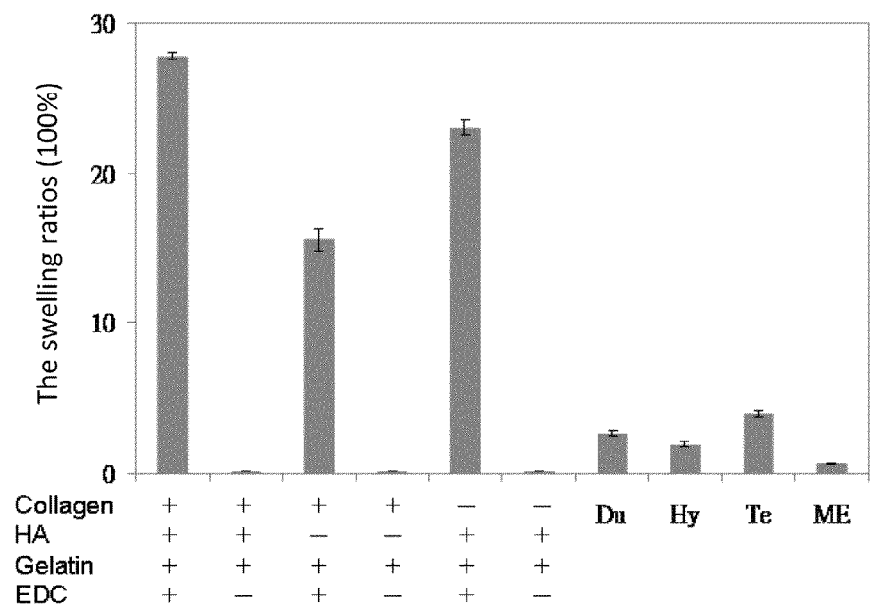
FIG. 2 illustrates the swelling studies of the scaffolds fabricated with collagen, HA, or gelatin or crosslinked via EDC (50 mM) (n=3). Without EDC crosslinking reactions, the scaffolds were dissoluble into water (symbol:x). Compared with commercial materials include, Du (DuoDERM 9C52552), Hy (Hydro Coll), Te (Tegaderm M1635), and ME (MEDPOR®).

The water absorption is necessary for the cell growth to gain vital nutritions. The absorption ratios were showed in FIG. 2. Three components crosslinked with EDC presented the absorption ability was about 15 to 30 times of dried scaffold, so did HA and gelatin. Without HA, the absorption ability was decreased to 15 times, which indicate HA was a significant factor with high water absorption property and was consistent to common knowledge. Although the scaffold of only HA and gelatin showed high swelling ratio, collagen is an important component in dermis. Therefore, the collagen was also adopted for fabricating scaffold. The concentrations of three components were reduced to evaluate the influence on swelling ratio. The results didn't show significant changes in the water adsorptions. Without crosslinking reaction, scaffolds were dissolved into water and couldn't measure the absorption abilities. Four commercial skin dressings were applied for comparing and all their swelling ratios were less than 10 folds. This revealed that the sponge-like scaffold retained large porous lamellar matrix spaces to increase their water-containing capacity. In general, three components had a large number of negatively charged carboxylic groups in their backbone, and were hydrophilic.

Evaluating the Degradation Rate of the Biomaterial by Lysozyme, Collagenase and Hyaluronidase The biomaterials (n=6) were accurately weighted and immersed in 1 ml of 0.1 M Tris-HCl with 0.05 M $CaCl_2$ (pH 7.4) containing 10 and 20 U collagenase I (Sigma) at 37° C. A total of 0.2 ml of 0.25 Methylenediamine tetraacetic acid (EDTA) was added to terminate the digestion after specific time intervals. The remaining scaffold were washed three times in distilled water and finally lyophilized. The biomaterial degradation was determined by the weight of residual scaffold, and expressed as a percentage of the original weight. Similar protocols were applied to hyaluronidase and lysozyme. Scaffold samples was suspended in PBS (pH=7.4) containing 30 or 50 U/ml hyaluronidase, incubated at 37° C. for 1, 3, 5, and 7 days. By incubating the scaffolds in PBS (pH 7.4) with lysozyme (10,000 and 30,000 U/ml), at 37° C. up to 21 days, the degradation of the biomaterial was tested by lysozyme. At the end of the degradation period, the samples were removed and washed for performing the following measurement. The degradation rates of the non-crosslinked biomaterial (n=6) were calculated by dividing the remaining weight of the biomaterial for comparative analysis to the initial weight of the biomaterial.

Figure 3:
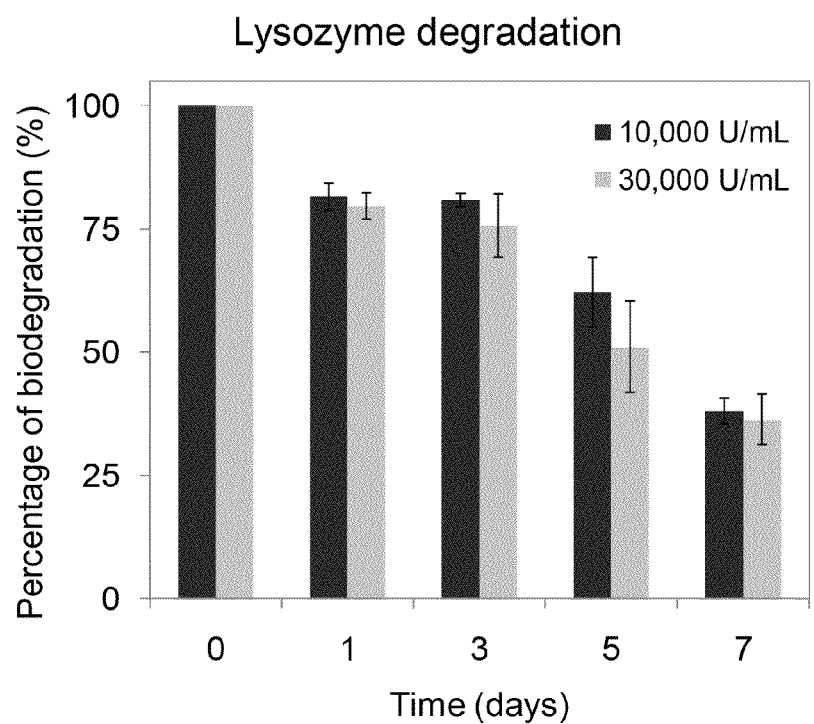
FIG. 3 illustrates the degradation rates of lysozyme (A), hyaluronidase (B), and collagenase (C).
Figure 3:
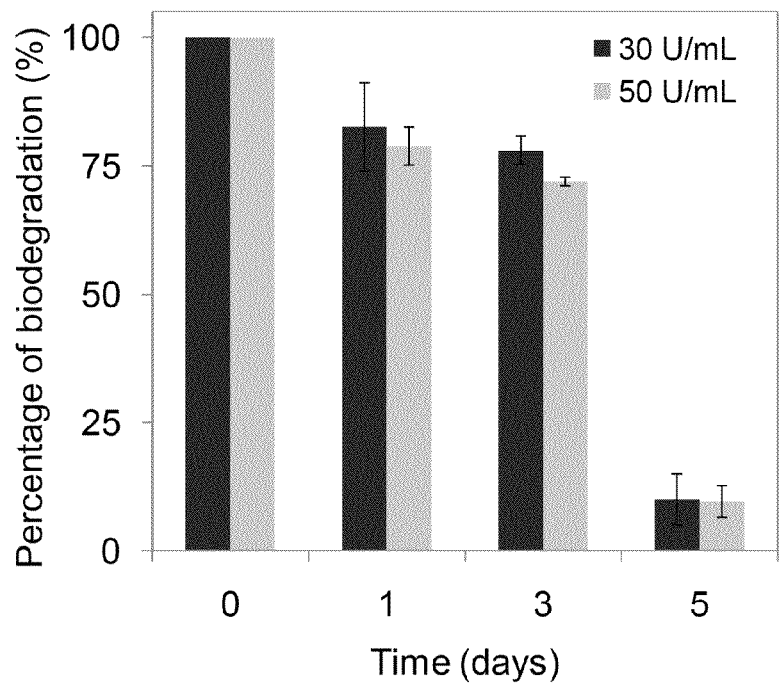
Figure 3:
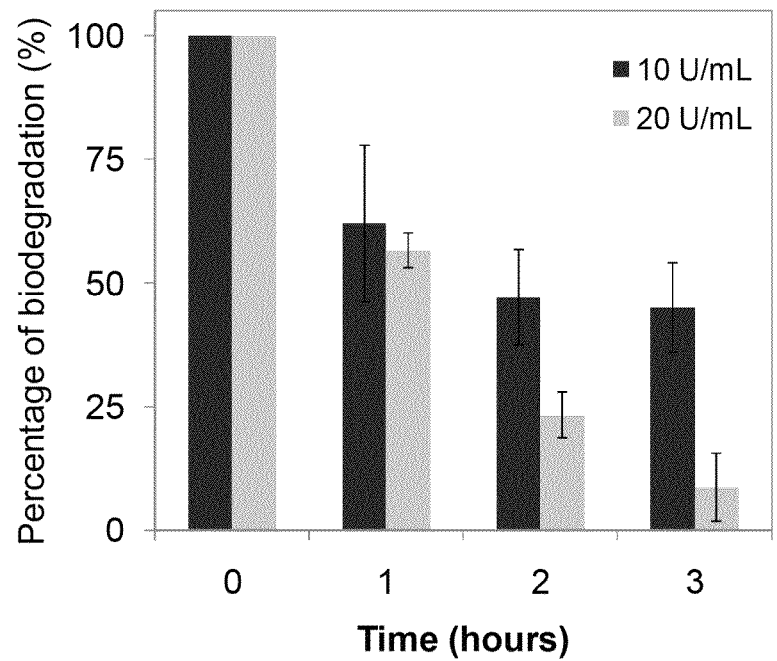

The biological stability of the collagen/HA/gelatin was tested by in vitro degradation test with lysozyme, hyaluronidase, and collagenase separately. As shown in FIG. 3A, the biomaterial was not fully degraded by 30,000 U/ml of lysozyme after 7 days. In FIG. 3B, the biomaterial was fully degraded by both 30 and 50 U/ml of hyaluronidase after 7 days. The biomaterial was fully degraded after incubated in 20 U/ml collagenase for 3 hours (FIG. 3C).

Example 2

Cell Grows within Porous Scaffold
Human Skin Primary Cultures

Human keratinocytes were cultured from foreskin primary culture, which was obtained from Chung-Ho Memorial Hospital, Kaohsiung Medical University, Taiwan. Human keratinocytes were cultured in Keratinocyte-SFM (10724; GIBCO™), supplemented with Bovine Pituitary Extract (BPE, Cat No. 13028-014), and EGF Human Recombinant (Cat No. 10450-013). The medium and growth supplement for keratinocytes contained γ-epidermal growth factor, BPE, insulin, fibroblast growth factor and calcium (0.09 mM). Neonatal foreskin primary human epidermal melanocytes (HEMn-MP) were purchased from Cascade Biologics™, cultured in Medium 254 (M-254-500; Cascade Biologics™), and supplemented with human melanocyte growth supplement (HMGS, Cat No. S-002-5). The Medium 254 was a basal medium containing essential and non-essential amino acids, vitamins, organic compounds, trace minerals, and inorganic salts. The human melanocyte growth supplement contained bovine pituitary extract, fetal bovine serum, bovine insulin, bovine transferrin, basic fibroblast growth factor, hydrocortisone, heparin, and phorbol 12-myristate 13-acetate. The primary cultures of human skin fibroblasts were complimentary gifts from Dr. Ching-Ying Wu (Department of Dermatology, Graduate Institute of Medicine, Center of Excellence for Environmental Medicine, Kaohsiung Medical University). All types of cells were incubated at 37° C. in a humidified incubator 5% $CO_2$ atmosphere.

Trypan Blue Assay

All cells were trypsinized with trypsin-EDTA 1× in phosphate-buffered saline (PBS) (BioWest) and aseptically diluted 0.5 ml into PBS and 0.5 ml of a solution trypan blue (0.4% w/v) is added. The stained cells were sampled with a Pasteur pipette and delivered to a hemocytometer by capillary action. A total of at least 500 cells were counted and the blue cells were counted separately.

Cell Attachment Rate and Viability

The scaffolds were sterilized with ethylene oxide gas, prewetted to exclude the remaining ethylene oxide and then placed in 24-well plates. A 100 μl of ($5\times10^5$ cells/$100_{10}$) cell suspension was loaded onto the top surface of each prewetted scaffold and allowed to penetrate into the scaffold. The cells/scaffold constructs were then incubated at 37° C. under 5% $CO_2$ condition for 4 hours for cell adherence. After cell adherence, the cells/scaffold constructs were transferred to a new 24-well plate in order to remove the lost cells at the bottom of the wells, and 0.5 ml of culture media was added in each new well containing the cells/scaffold construct. Culture media was changed every 2 days and culture plates were shaken during culture. At every indicated time interval, cells/scaffold constructs were collected for further experimental analysis.

3-(4,5-dimethylthiazol-2-yl)-5-(3-carboxymethoxyphenyl)-2-(4-sulfophenyl)-2H-tetrazolium (MTS) assay was used to study the cell viabilities and proliferation rate of cells seeded on the scaffolds (Han et al., *Breast Cancer Res* 11, R57 (2009)). MTS assay was taken up by live cells, reduced by the dehydrogenase enzymes and released back into the culture medium as a yellow formazan product. The amount of formazan product, measured by absorbance at 490 nm, was directly proportional to the number of living cells in the culture. The cells in 100 μl medium were exposed to 20 μl of CellTiter 96 AQueous One Solution (Promega, Cat No. G3582) for 3 hours according to the manufacturers' instructions. Absorbance at 490 nm was recorded using a spectrometer plate reader.

Figure 4:
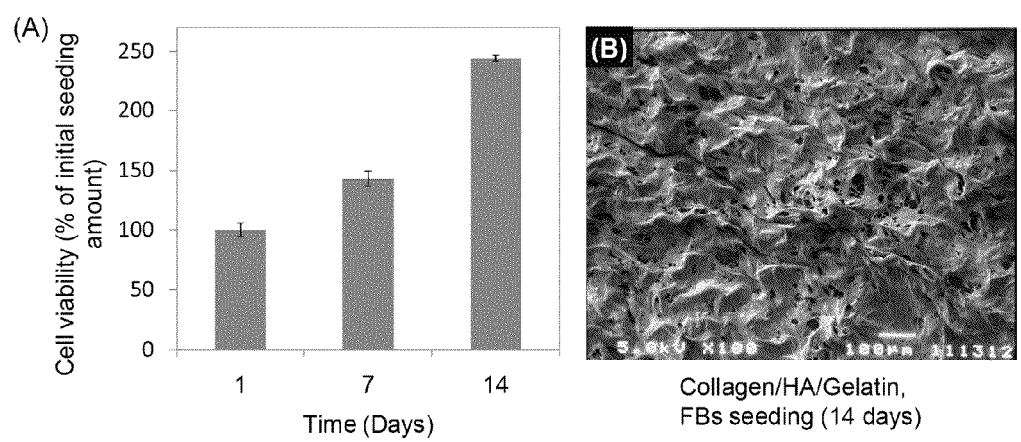
FIG. 4 illustrates the cell proliferation ratios of human skin FBs seeded in the scaffolds (n=4). From 1 to 14 days, the proliferation rate could be observed by MTT assay (A). The SEM image of FBs seeding in scaffold for 14 days (B).

To assure attachment rate of cells on the scaffold, the cytocompatibility of human fibroblasts seeded within scaffold was studied by testing the cell viability. As comparing to the same amount of cells seeded on 24 well plates directly, it demonstrated that about 75% of the cells seeded attached to the scaffold successfully (FIG. 4A). The human fibroblasts viable cell numbers on sponge-like scaffolds were measured by MTS assay. At 14 days post-seeding culture, the cell density of fibroblasts grown within the scaffold demonstrated a major enhancement, indicating the scaffold made of the biomaterial of the present invention had the advantages of the cell proliferation, differentiation and survivability.

Morphology of Porous Scaffold/Biomaterial (SEM Images)

The morphological characteristics of porous scaffolds were observed by using scanning electron microscopic image (SEM, JEOL, Tokyo, Japan). The scaffolds were fixed in 2.5% glutaraldehyde in 0.1 M sodium phosphate buffer, pH 7.2 overnight, and post-fixed in 1% osmium tetroxide for 1 hour, dehydrated in ethanol (30, 50, 75, and 99.5%) and critical-point dried. The dried samples were coated with gold via a sputter-coater at ambient temperature. Micrographs of scaffolds were taken at suitable size (100×, and 200×). The pore size distribution was determined by Beckman Coulter LS32 equipment with a range of 0.01 μm to 1000 μm. The pore size of 30 pores on each SEM photos and totally 5 SEM photos were measured then the average pore size was calculated.

The morphological characteristic of the collagen/HA/gelatin scaffolds recorded by SEM was shown in FIG. 4B. The scaffolds revealed interconnected highly porous structures and the pore wall surface of untreated with fibroblasts appeared smooth and homogeneous. The SEM image of sponge-like scaffold indicated that they had open macroporous structures with pore size in the range of 132.5±8.4 nm. For fibroblasts cell-treatment scaffold (14 days), the SEM image was shown in FIG. 4B. The pore wall surfaces of the cell-treatment scaffolds were characterized to be rough and be composed of fractures, which were presumably degraded by fibroblasts.

Co-Cultures for 3D Human Skin Cell
In Vitro Cell Culture and Fluorescent Studies To detect the skin distribution, the cells were stained with PKH67 before seeding within the scaffold. Cells were incubated with 5 μM PKH-67 (a green fluorescent compound that incorporates aliphatic reporter molecules into the cell membrane by selective partitioning; Sigma-Aldrich) for 5 min at 25° C. and gently vortexed every 30 s (according to the manufacturer's protocol). Unincorporated PKH-67 was removed by washing the cells with complete medium. PKH-67-labeled cells were replated on a scaffold surface at a density of $1 \times 10^5/cm^2$ and then harvested at various culture period intervals.

Figure 5:
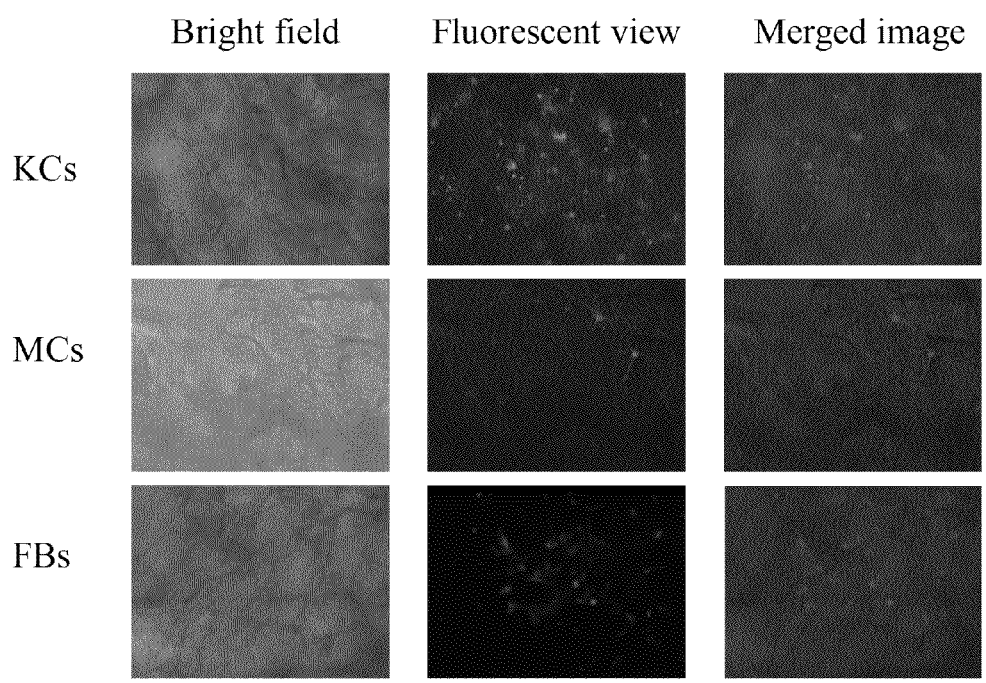
FIG. 5 illustrates the photographed human KCs, MCs and FBs cultured in the scaffold on bright field, fluorescent and merged phase. Fluorescent compound, PKH-67 (green), was used to stain cells.

The culture of human skin cells within collagen/HA/gelatin scaffold were studied by fluorescent microscope after fluorescent staining. (FIG. 5) Three kinds of skin cells were all normally proliferated under the existence of collagen/HA/gelatin scaffold which the materials were proven to have benefits for cell growth. The degree of cross-linking has been confirmed to be related to the distribution of the porous structure in the scaffold and water containing ability. The scaffold formed from the biomaterial had appropriate pore size and water adsorption ability for human skin cell growth.

Immunofluorescence Study of the Skin Equivalent Paraffin Section

Human skin equivalents were generated by seeding $10^6$ keratinocytes and $10^5$ melanocytes on the scaffold with $5 \times 10^5$ fibroblasts seeded on for 7 days in advance. After keratinocytes and melanocytes were seeded, the cells were incubated for another 7 days and mediums were changed every 2 days. During co-culture, the medium were mixed with the same ratio to cell amount.

The protocols were followed the published protocols with minor modifications (Dainiak et al., *Biomaterials* 31, 67-76 (2010); Wu et al., *Biomaterials* 31, 631-640 (2010)). Specimens of the scaffold with keratinocytes, melanocytes, and fibroblasts co-cultured on were fixed with 4% formaldehyde prepared in PBS for 24 hours at room temperature. The specimens were embedded in paraffin, and cut into 5 μm sections. Sections were dewaxed, then permeabilized with 3% $H_2O_2$ in PBS for 15 min at room temperature, then blocked with fibroblasts for 1 hour and incubated with primary antibodies to cytokeratin (for keratinocytes) or to s-100 (for melanocytes). Sections were then washed and incubated with cy3-conjugated goat anti-rabbit antibody (Millipore) and FITC-conjugated goat anti-mouse antibody (Millipore) for 30 min at room temperature and counterstained with 4,6-diamidino-2-phenylindole (DAPI) (Vector, Burlingame, Calif.). Immunofluorescent images were taken (TE300; Nikon, Japan). Sections were also stained with hematoxylin and eosin (H & E stain) to check the localization of cells.

Figure 6:
FIG. 6 illustrates the protocols of 3D human skin equivalent (A). (B) Paraffin section of the 3D human skin equivalent under microscope in bright view (400×). (C-E) Fluorescent images of KCs, MCs, and FBs cultured in scaffold for 14 days, and were stained with DAPI (blue); anti-cytokeratin to mark KCs (green); anti-s-100 for MCs (red). (F) The merged image was of KCs, MCs, and FBs together. Arrows pointed to KCs, MCs, and FBs with specific colors.
Figure 6:
Figure 6:
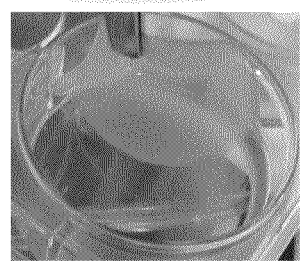
Figure 6:
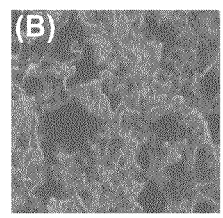
Figure 6:
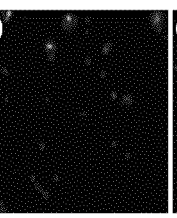
Figure 6:
Figure 6:
Figure 6:
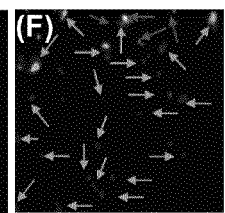

To construct a model which can simulate real human skin conditions, co-culture protocols for 3D human skin equivalent were constructed (FIG. 6A). The skin equivalent was generated by seeding keratinocytes and melanocytes on the scaffold with fibroblasts seeded on for 7 days in advance. After incubating the co-cultured cells for another 7 days, the samples were vertically sectioned and stained with immunofluorescence and observed under the microscope. In FIG. 6B, it was the paraffin section of the skin equivalent under bright field. The FIG. 6C showed the cells stained with DAPI. And in FIG. 6D, the keratinocytes were marked with anti-cytokeratin, FITC conjugated. The keratinocytes showed green fluorescence. In FIG. 6E, melanocytes were stained with anti-s 100 protein, cy3 conjugated, showed red color. And the images of FIG. 6C-E were merged together to appear FIG. 6F. As shown in FIG. 6F, melanocytes and keratinocytes distributed above, and the cells stained with DAPI but not by anti-cytokeratin or anti-s 100 protein were fibroblasts.

Collagen Amount

For measurement of total collagen amount synthesized by fibroblasts in scaffold, Sirius Red dye (Direct Red; Sigma) was used to stain total collagen. The collagen secreted by fibroblasts incubated on 48 well plates or in the scaffold and co-culturing of fibroblasts, keratinocytes, and melanocytes on 2D well surface or in the scaffold were compared. After indicated time interval, mediums were removed and cells washed with PBS twice. 100 μl of 0.1% Sirius Red stain (0.05 g Sirius Red powder per 50 ml picric acid) was added to each well and kept at room temperature for 1 h. The unattached stain was removed and washed for five times with 200 μl of 0.1 N HCl. The attached stain was extracted with 100 μl of 0.1 N NaOH (15 min) and mixed well. The stain was placed into 96 well plate to read the absorbance at 540 nm using a microplate reader.

Figure 7:
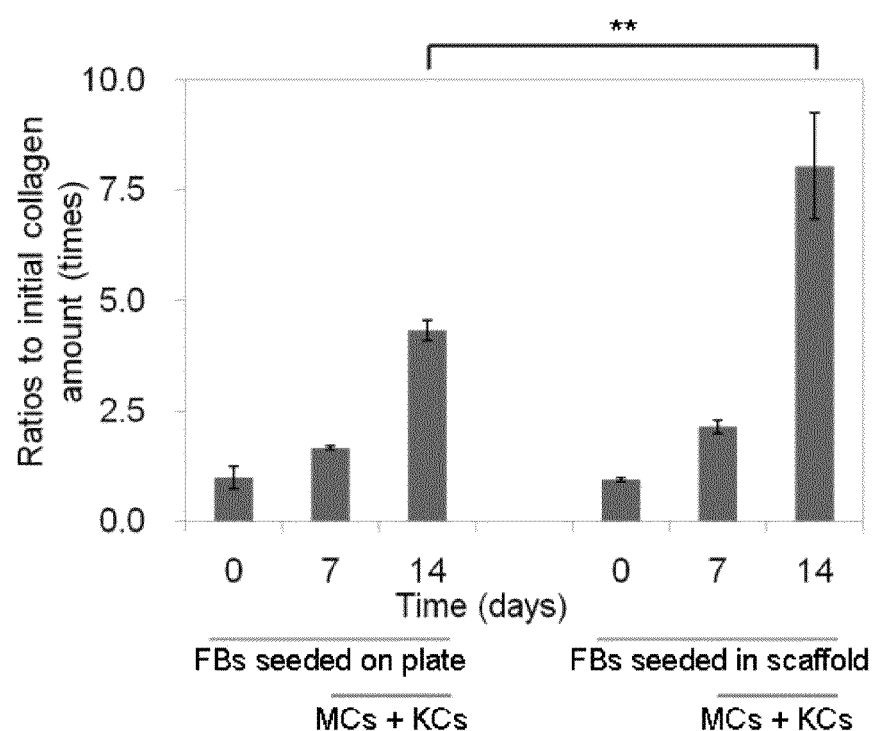
FIG. 7 illustrates the collagen amount secreted from FBs seeded on plate or with the scaffold. On the plate or in the scaffold, FBs raised for the first 7 days, after that, KCs and MCs seeded in for another 7 days.

Collagen in ECM imparts appropriate mechanical strength to the tissue and the effect of collagen to the production of ECM by fibroblasts is also important. Sirius Red dye was used to stain the collagen both in the scaffold and which secreted by fibroblasts. The collagen amount of scaffold only, fibroblasts raised inside the scaffold for 7 days, and the amount of collagen with fibroblasts seeded in the 48 well plates for 7 days, and scaffold with fibroblasts seeded for 7 days, keratinocytes and melanocytes seeded in for another 7 days were compared to examine if keratinocytes and melanocytes affect collagen secretion by fibroblasts. In FIG. 7, as seeding fibroblasts in the scaffold, the collagen secreted by fibroblasts is about 30% more than seeded on the well. Collagen is an important component of extacellular matrix (ECM), and cell proliferation, tissue body formation, and tissue body shape were dependent on collagen concentrations. Therefore, to detect the probability of wound healing promotion the secretion amount of collagen is an important index. As the scaffold had the potential to promote collagen secretion of fibroblasts, it may be a good material for tissue engineering on wound healing.

Example 3

Wound Healing in Rat Model
Animal Preparation

Male Wistar rats (250-285 g) were used for all experiments in this study. The rats were housed in Plexiglas cages in a temperature-controlled (22±1° C.) room, on a 12-hour/12-hour light/dark schedule, and with free access to food and water. Six rats were randomly divided into 2 groups, injury and treatment group. The excision wound healing test was modified from (Huang and Yang, *Int J Pharm* 346, 38-46 (2008)). Following anaesthetized dorsal hair was shaved by electric razor, a full thickness excisions of 2 cm in diameter were created with a surgical knife. After excision was made, the biomaterial of equal size was rinsed by saline, and covered on the wound immediately. For injury group, wounds were not covered for comparison. After surgery, rats were placed in individual cages for recovery.

Evaluation of the Wound Size

Photographs were taken at the 1, 2, 3, 4, 5, 7 and 10 days after injury using digital camera (Coolpix P6000, Nikon, Japan) with same parameters (F7.2, 1/60). SPOT (Diagnostic Instruments, Inc., Sterling Heights, Mich., USA) software was used to measure the area of each wound. The degree of wound healing was expressed as the percentage of wound area, calculated as (wound area of day $N$/wound area of day 0)×100%.

Figure 8:
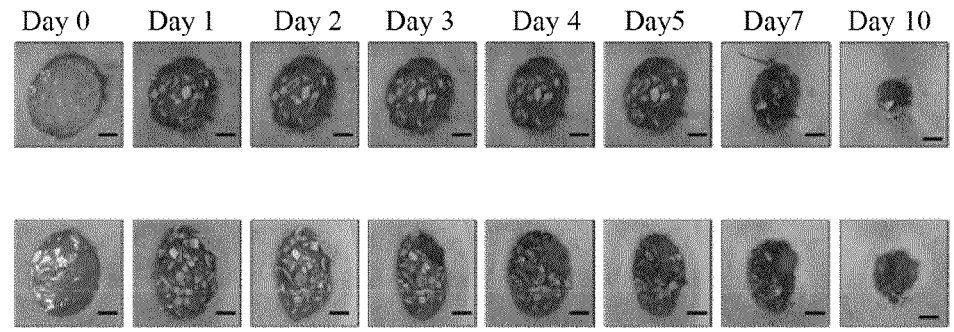
FIG. 8 illustrates the healing pattern of scaffold treated (A, top) and injury (A, bottom) wound after 0, 1, 2, 3, 4, 5, 7 and 10 days after injury. The wound healing efficacy of the scaffold was evaluated in a full thickness wound model. Following anaesthetized a full thickness excisions of 2 cm in diameter were created by a surgical knife of male Wistar rats. For treatment group after excision was made, the scaffold was covered on the wound immediately. For injury group wounds were not covered for comparison. From the first day after injury, the healing of wound from injury group was slower than scaffold treated wound until 10 days after injury. Scale bar=0.5 cm. (B) Wound contraction ratios of scaffold and injury at different times. By examining the wound area at definite days, the reduction of wound area was calculated. The surface area of the burn wounds was calculated as described in methods. The wound area decreased rapidly in the presence of scaffold when compared with the control since first day after injury. The wound area in control group was 60% of the original size on day 7. This percentage was reached almost 3 days earlier at scaffold group. The difference between wounds of injury and scaffold group were statistically significant at day 10. Data are presented as the mean±standard error of the mean (SEM) A significant difference compare to injury group was defined as $P<0.05$.*Significant.
Figure 8:
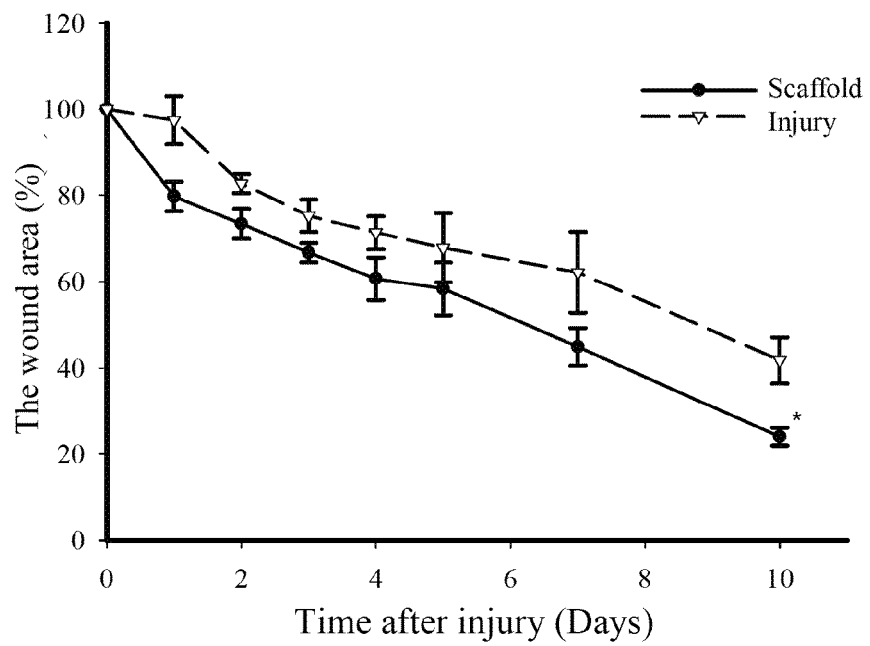

The wound healing efficiency of the scaffold was evaluated in a full thickness wound model. The wound area of both injury and treatment group shrank with the time (FIG. 8). Wound area of treatment group at 1, 2, 3, 4, 5, and 7 days after injury was 79.7±3.4%, 73.4±3.5%, 66.8±2.2%, 60.7±5.0%, 58.3±6.1% and 44.9±4.3% respectively, which are all smaller than wound area of injury group (97.4±5.5%, 86.3±2.2%, 75.3±3.7%, 71.4±3.8%, 67.9±8.1% and 62.2±9.4%). Since one day after injury the wound area of treatment group was smaller than injury group's wounds, this trend was consistent to 10 days after injury. Wounds of treatment group were closure faster than wounds of injury group. At the 10th day after injury, the area of wound with scaffold was 24.0±2.1%, where the wound area of injury group was 41.8±5.3%, this scaffold could significantly increase wound closure speed. Since the scaffold-treated wound healing achieved more than 45% wound closure in the first 7 days; almost 75% wound closure was achieved within 10 days.

Histological Study

Figure 9:
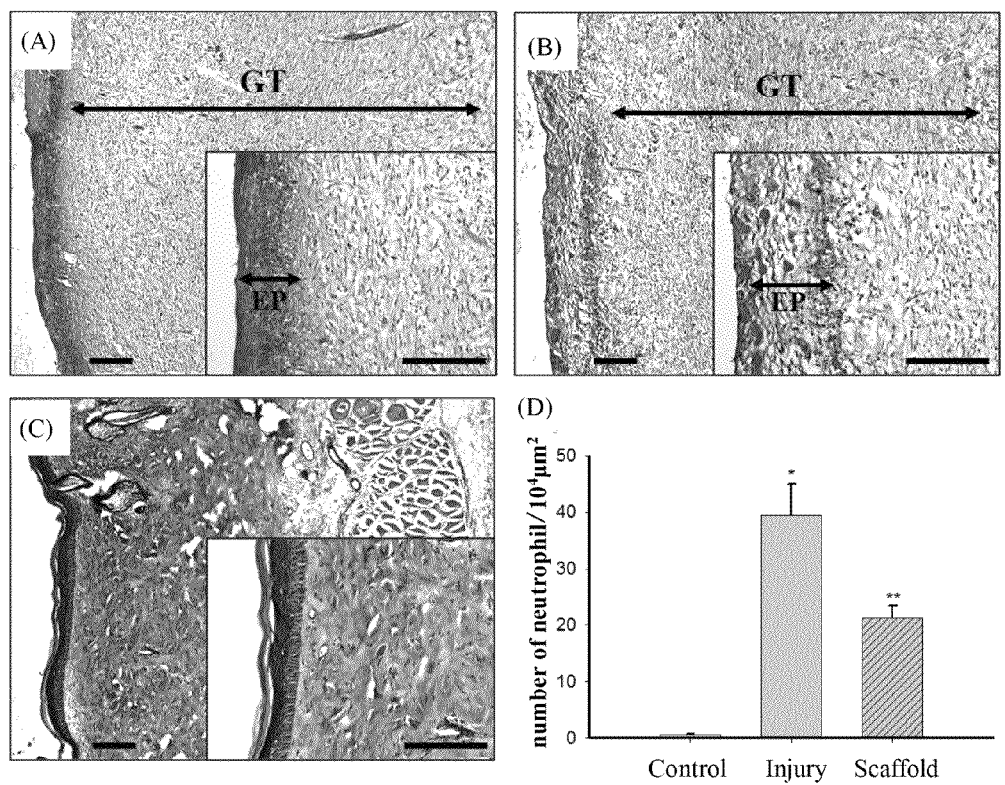
FIG. 9 illustrates the hematoxylin and eosin (H&E) stained sections for the morphological evaluation of skin wounds. Ten days after injury, rats were scarified, wound skin was fixing in 4% of paraformaldehyde. The skin was stained with H&E for histological observation. Ten randomly selected areas of dermis from each sample were examined at a magnification of 400× for counting neutrophil. Scaffold group (A), injury group (B) and control (C) wounds at 10 days after injury. Both scaffold and injury group wounds have granulation tissue. The epidermis of treatment group was denser than injury epidermis. Wounds of treatment group were had less neutrophil infiltrated compare to injury group (D). Scale bar=200 μm. EP, epithelial layer, GT, granulation tissue. *$p<0.05$ as compared with control group. **$p<0.05$ as compared with injury group and control group.

Histological exam of skin section after H&E stain (FIG. 9) indicated that in the skin of both treatment and injury groups granulation tissues were found, the scaffold did not interrupt wound healing. The epidermis of treatment group was denser than of injury group. The scaffold could enhance the strength of the skin during wound healing. Compared to injury group, wounds of treatment group were less neutrophil infiltrated. During wound healing process, neutrophil would secret substances to accelerate keratinocyte differentiation and delayed wound closure. By applying this scaffold, neutrophil infiltration would be decreased and accelerate wound closures.

This scaffold can improve healing speed, increase density of epidermis and less neutrophil infiltrated. These evidences indicated that this scaffold is suitable for excision wound healing.

Ten days after injury, rats were scarified by over anaesthetized. Wound skin was fixed in 4% of paraformaldehyde. The skin was stained with hematoxylin and eosin (H&E) for histological observation. For histological analysis images were captured with a Spot Xplorer CCD integrating camera (Diagnostic Instruments, Inc., Sterling Heights, Mich., USA) using a Leica DM-6000 microscope (Leica, Wetzlar, Germany). The histological analysis was modified from Bayat et al. (2005). 10 randomly selected areas of dermis from each sample were examined at a magnification of 400× for counting neutrophils. Histological examinations were performed in a blind fashion.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A biomaterial comprising a scaffold consisting of collagen, hyaluronic acid, and gelatin, wherein (1) collagen, hyaluronic acid, and gelatin are cross-linked via ethyl-3-[3-dimethylaminopropyl] carbodiimide (EDC); (2) the scaffold has the following structure:

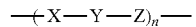

wherein X is gelatin-gelatin, gelatin-collagen, or gelatin-hyaluronic acid; Y is collagen-collagen, collagen-gelatin, or collagen-hyaluronic acid; Z is hyaluronic acid-gelatin, hyaluronic acid-collagen, or hyaluronic acid-hyaluronic acid; and n is an integer of 1 or more than 1; (3) the percentage of the collagen is 30% to 45%, the percentage of the hyaluronic acid is 0.1% to 5%, and the percentage of the gelatin is 50% to 70%, provided that total percentage of collagen, hyaluronic acid, and gelatin is 100%; and (4) the biomaterial has a swelling ratio more than 20 fold of dried scaffold.

2. The biomaterial of claim 1, which is a porous, three-dimensional biomaterial.

3. The biomaterial of claim 1, which has a pore size of 10 to 500 μm.

4. The biomaterial of claim 3, wherein the pore size is 50 to 200 μm.

5. The biomaterial of claim 1, which further comprises fibroblasts, keratinocytes, and melanocytes.

* * * * *